Figure 1:
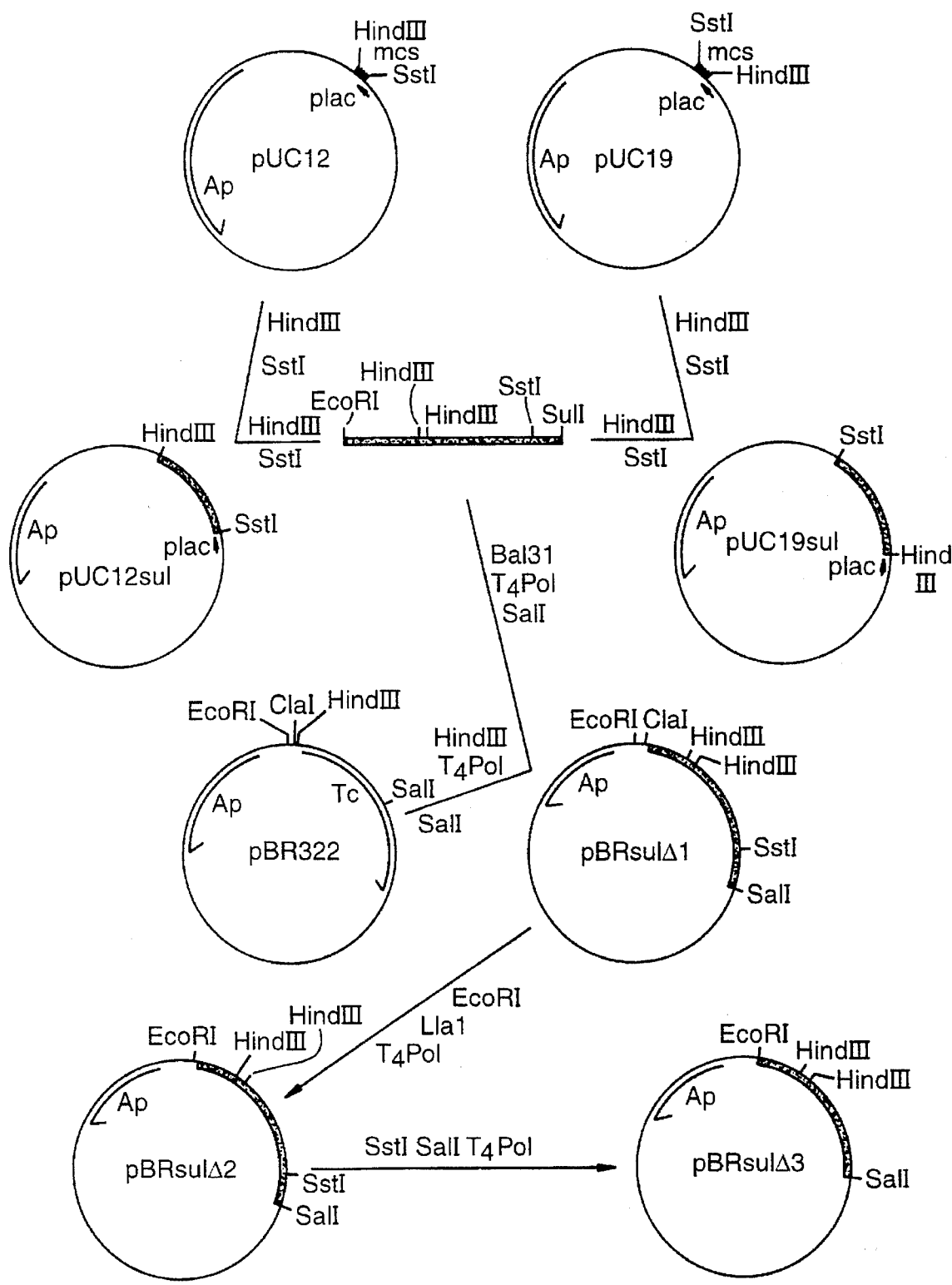

US005633444A

United States Patent [19]
Guerineau et al.

[11] Patent Number: 5,633,444
[45] Date of Patent: May 27, 1997

[54] SULFONAMIDE RESISTANCE GENES AND THEIR USE

[75] Inventors: Jean F. Guerineau, Dundee; Philip M. Mullineaux, Norwich; Edgar W. Parnell, Odgar, all of United Kingdom

[73] Assignee: Rhone-Poulenc Agrochimie Limited, Lyons, Cedex, France

[21] Appl. No.: 444,420

[22] Filed: May 19, 1995

Related U.S. Application Data

[63] Continuation of Ser. No. 102,395, Aug. 5, 1993, abandoned, which is a continuation of Ser. No. 985,352, Dec. 1, 1992, abandoned, which is a continuation of Ser. No. 746,306, Aug. 14, 1991, abandoned, which is a continuation of Ser. No. 429,227, Oct. 31, 1989, abandoned.

[30] Foreign Application Priority Data

Oct. 31, 1988 [GB] United Kingdom .................... 8825402

[51] Int. Cl.$^6$ .............................. A01H 4/00; C12N 5/14
[52] U.S. Cl. ................. 800/205; 800/255; 800/DIG. 43; 800/DIG. 17; 435/414; 435/418; 435/419; 504/214
[58] Field of Search ......................... 501/214; 435/172.3, 435/240.4; 536/23.7; 800/205, 255, DIG. 43

[56] References Cited

U.S. PATENT DOCUMENTS

| | | | |
|---|---|---|---|
| 4,626,505 | 12/1986 | Falco | 435/172.3 |
| 4,724,039 | 2/1988 | Hillemann | 504/214 |
| 4,757,011 | 7/1988 | Chaleff et al. | 435/172.3 |
| 4,774,381 | 9/1988 | Chaleff et al. | 800/230 |

FOREIGN PATENT DOCUMENTS

| | | | |
|---|---|---|---|
| 0154204 | 9/1985 | European Pat. Off. . | |
| 0218571 | 4/1987 | European Pat. Off. | 435/172.3 |
| 0240250 | 10/1987 | European Pat. Off. . | |
| 0257993 | 3/1988 | European Pat. Off. . | |
| 0154204 | 9/1995 | European Pat. Off. . | |
| WO87/05629 | 9/1987 | WIPO . | |
| WO90/10076 | 9/1990 | WIPO . | |

OTHER PUBLICATIONS

Sundström et al., *Mol. Gen. Genet.* (1988) 213:191–201.
Ward et al., *Plasmid* (1982) 7:239–250.
Kidd et al., *Plant Science Letters* (1982) 26:211–217.
Anderson et al., *Biochem. J.* (1986) 240:709–715.
Cossins, "Biochemistry of Plants" vol. No. 2, Academic Press (1980) Davies, ed., chapter 9, pp. 365–415.
Gil et al., *Gene* (1983) 25:119–132.
Guerineau et al., *Nucleic Acids Res.* (1989) 17(11):4370.
Guerineau et al., *Nucleic Acids Res.* (1988) 16(23):11380.
Mazur et al., *Abstr. Pap. Am. Chem. Soc.* (1988) 196(o):AR-GO–ISO.
Merrick et al., *Plant Science Letters* (1981) 20:291–296.
Swedberg et al., *L. Bacteriology* (1979) 137(1):129–136.
Veerasekaran et al., *Pestic. Sci.* (1981) 12:325–329.
Veerasekaran et al., Pestic. Sci. (1981) 12:330–338.

Comai, et al (1988) The Journ. Biol. Chem. 263 (29):15104–15109.
Boswell et al in Computational Molecular Biology (Lesk, ed.) Oxford University Press, Oxford, 1988, pp. 170–171.
Ellis, et al (1987) EMBO J. 6 (1):11–16.
Gelvin (1987) Plant Molecular Biology 8:355–359.
Brown, et al. (1981) Plasmid 5:188–201.
Lopez et al (Sep. 1987) Journal of Bacteriology 169(9):4320–4326.
Della-Croppa, et al. (1987) Bio/Technology 5:579–584.
Gifford, et al (1986) Weed Research 26: 389–396.
Carramolino et al (1989) Gene 77: 31–38.
Kay et al (Jun. 1987) Science 236: 1299–1302.
Ellis et al., "Maize Adh–1 promoter sequences control anaerobic regulation: Addition of upstream promoter elements from constitutitve genes is necessary for expression in tobacco" *EMBO J.* (1987) 6:11–16.
Gelvin, "Biotechnology news and views" *Plant Mol. Biol.* (1987) 8:355–359.
Brown et al., "A physical map of the IncN plasmid R46" *Plasmid* (1981) 5:188–201.
Lopez et al., "Sulfonamide resistance in *Streptococcus pneumoniae*: DNA sequence of the gene encoding dihydropteroate synthase and characterization of the enzyme" *J. Bacteriol.* (1987) 169:4320–4326.
della-Cioppa et al., "Targeting a herbicide–resistant enzyme from *Escherichia coli* to chloroplastss of higher plants" *Bio/Technology* (1987) 5:579–584.
Giffard et al., "Enhancement of asulam resistance in barley" *Weed Res.* (1986) 26:389–396.

(List continued on next page.)

*Primary Examiner*—Che S. Chereskin
*Attorney, Agent, or Firm*—Morrison & Foerster LLP

[57] ABSTRACT

Plant cells are transformed by:
(i) transforming a plant cell whose growth is sensitive to inhibition by a sulfonamide or a salt thereof with a chimaeric gene comprising (a) a plant promoter, (b) a sulfonamide resistance gene having a sequence encoding a transit peptide fused to the 5'-end of the resistance gene and (c) a plant polyadenylation/terminator sequence;
(ii) selecting a transformed plant cell whose growth is resistant to inhibition by a sulfonamide or salt thereof;
(iii) optionally, regenerating from the transformed plant cell a genetically transformed plant which exhibit the said resistance;
(iv) optionally, obtaining seed from the regenerated plant; and
(v) optionally, propagating plants from the seed.

The growth of weeds can be controlled by a locus where a transgenic plant obtained as above is being cultivated by applying to the locus an effective amount of a herbicide, such as asulam, which acts by inhibiting dihydropteroate synthase. The sulfonamide resistance gene can be also used as a selectable marker. The sequence of a sulfonamide resistance gene is presented.

21 Claims, 8 Drawing Sheets

OTHER PUBLICATIONS

Carramolino et al., "Transformation of Penicillium chrysogenum to sulfonamide resistance" *Gene* (1989) 77:31–38.

Kay et al., "Duplication of CaMV 35S promoter sequences creates a strong enhancer for plant genes" *Science* (1987) 236:1299–1302.

Sundström et al., "Site–specific recombination promotes linkage between trimethoprim— and sulfonamide resistance genes. Sequence characterization of *dhfrV* and *sulI* and a recombination active locus of Tn21" *Mol. Gen. Genet.* (1988) 213:191–201.

Ward et al., "Physical and genetic analysis of the Inc–W group plasmids R388, Sa and R7K" *Plasmid* (1982) 7:239–250.

Kidd et al., "The effect of asulam on purine biosynthesis" *Plant Sci. Lett.* (1982) 26:211–217.

Anderson et al., "Synthesis of the small subunit of ribulose-–bisphosphate carboxylase from genes cloned into plasmids containing the SP6 promoter" *Biochem. J.* (1986) 240:709–715.

Cossins, "One–carbon metabolism" *biochemistry of Plants* (1980) Academic Press, Davies, ed., vol. 2, Chapter 9, pp. 365–415.

Gill et al., "Cloning and expression of a p–aminobenzoic acid synthetase gene of the candicidin–producing *Streptomyces griseus*" *Gene* (1983) 25:119–132.

Guerineau et al., "Nucleotide sequence of the sulfonamide resistance gene from plasmid R46" *Nucl. Acid Res.* (1989) 17:4370.

Guerineau et al., "An expression cassette for targeting proteins into chloroplasts" *Nucl. Acids Res.* (1989) 16:11380.

Mazur et al., "Herbicide resistant plants carrying mutated acetolactate synthase genes" *Abstr. Pap. Am. Chem Soc.* (1988) 96:ARGO–ISO.

Merrick et al., "Selection for asulam resistance in tissue cultures of celery" *Plant Sci.* (1981) 20:291–296.

Swedberg et al., "Characterization of mutationally altered dihydropteroate synthase and its ability to form a sulfonamide–containing dihydrofolate analog" *J. Bacteriol.* (1979) 137:129–136.

Veerasekaran et al., "Studies of the mechanism of action of asulam in plants. Part I: Antagonistic interaction of asulam and 4–aminobenzoic acid" *Pestic. Sci.* (1981) 12:325–329.

Veerasekaran et al., "Studies of the mechanism of action of asulam in plants. Part II: Effect of asulam on the biosynthesis of folic acid" *Pestic. Sci.* (1981) 12:330–338.

Comai et al., "Chloroplast transport of a ribulose bisphosphate carboxylase small subunit–5–enolpyruvyl 3–phosphoshikimate synthase chimeric protein requires part of the mature small subunit in addition to the transit peptide" *J. Biol. Chem.* (1988) 263:15104–15109.

Boswell et al., "Sequence comparison and alignment: the measurement and interpretation of sequence similarity" *Computational Molecular Biology* (1988) Oxford University Press, Lesk, ed., Chapter 14, pp. 169–171.

De Block, "Genotype–independent leaf disc transformation of potato (*Solanum tuberosum*) using *Agrobacterium tumefaciens*" *Theor. Appl. Genet.* (1988) 76:767–774.

Lubben et al., "Chloroplast import characteristics of chimeric proteins" *Plant Mol. Biol.* (1989) 12:13–18.

Maliga et al., "Improved expression of streptomycin resistance in plants due to a deletion in the streptomycin phosphotransferase coding sequence" *Mol. Gen. Genet.* (1988) 214:456–459.

Product Brochure for *Asulox® Herbicide Use In Temperature Climates* Rhône–Poulenc Agronchemicals, 2 pages total.

TGGTGGCGTTACGCTGGTTTGTGGTCTTTTTGGCCTCTTTTTGTGTAGCAAGCGCGAGCAGCTATTTTTTC
          20                    40                    60
GTAGTGCTGTGCCGCCTCGCCGTGCCTTTCGCAGTGCACCGTGCCCAAGTTACGGTTATCCGTTT
        80                   100                   120                   140
TGGCTTCTGGCTCTAACATTCGGTCAAGCCGACCCGCCATTCGGCTTACCTCGCCCCGTTAGATGCACT
       160                   180                   200                   220
AAGCACATAATTGCTCACAGCCAAACTATCAGTTCAAGTCTGCTTTTATTTTTAAGCGTGCATAATAAGCCC
            240                   260                   280                   300
TACACAAATTGGGAGATATCATGAAAGGCTGGCTTTTTCTTGTTATCGCAATAGTTGGCGAAGTAATCGCAAC
          320                   340                   360
ATCCGCATTAAAATCTAGCGAGGGCTTTACTAAGCTTGTTGCTTGCTTGCCCCGTTGTCATAATCGGTTATGGCATCGC
                400                   420                   440
ATTTTATTTTCTTCTCTGGTTCTGAAATCCATCCCCTGTTGCTTATGCAGTCTGGGACTCGGCGT
       460                   480                   500                   520
CGTCATAATTACAGCCATTGCCTGGTTCATGGGCAAAAGCTTGATGCGTGGGGCTTTGTAGGTATGGGGCT
          540                   560                   580                   600
CATAATTGCTGCCTTTTTGCTCCGCCGATCCCCGATGAAGTCGCTGCGGAGGCCGACGCC ATG GTG ACG
              620                   640                   660                   680        M   V   T
                                                                                  720
GTG TTC GGC ATT CTG AAT CTC ACC GAG GAC TCC TTC TTC GAT GAG AGC CGG CGG CTA
 V   F   G   I   L   N   L   T   E   D   S   F   F   D   E   S   R   R   L
            740                              760                   780
GAC CCC GCC GGC GCT GTC ACC GCG ATC GCG GCG ATC GAA ATG CTG CGA GTC GGA TCA GAC GTC
 D   P   A   G   A   V   T   A   A   I   A   A   I   E   M   L   R   V   G   S   D   V
              800                           820                              840
GTG GAT GTC GGA CCG GCC GCC AGC CAT CCG GAC GCG AGG CCT GTA TCG CCG GAT
 V   D   V   G   P   A   A   S   H   P   D   A   R   P   V   S   P   A   D

FIG. 4A

FIG. 4B

```
GAG ATC AGA CGT ATT GCG CCG CTC TTA GAC GCC CTG TCC GAT CAG ATG CAC CGT GTT
 E   I   R   R   I   A   P   L   L   D   A   L   S   D   Q   M   H   R   V
         860             880             900
                                 920                     940

TCA ATC GAC AGC TTC CAA ATC CAA GGA TTT CCT GCG CGC TAT GCG AAG CTC CGC GGC GTG
 S   I   D   S   F   Q   I   Q   G   F   P   A   R   Y   A   K   L   R   G   V
 960                     980                     1000

TAC CTG AAC GAT ATC CAA CTG AGG GAC CTC TAT CCC GAT ATT GCT GAG
 Y   L   N   D   I   Q   L   R   D   L   Y   P   D   I   A   E
             1020                    1040                    1060

GCG GAC TGC AGG GTT ATG GTG GAA GAC GCA CAC TCA GCG CGG GAT GGC ATC GCC ACC CGC
 A   D   C   R   V   M   V   E   D   A   H   S   A   R   D   G   I   A   T   R
                     1080                    1100                    1120

ACC GGT CAC CTT CGA CCC CTT GAG ATT GTG CGG CTC TTC TTC GAG GCG
 T   G   H   L   R   P   L   E   I   V   R   L   F   F   E   A
     1140                    1160                    1180

CGG GTT TCC GCC TTG CGA GCT GCT GTC AAC GCC GAC CGG CTC ATC CTC GAT CCG
 R   V   S   A   L   R   A   A   V   N   A   D   R   L   I   L   D   P
                 1200                    1220                    1240

GGG ATG GGA TTT TTC AAG TCG GCG GCA CCG GAA ACA TCG TTG CTG GTG TCG AAC
 G   M   G   F   F   K   S   A   A   P   E   T   S   L   L   V   S   N
                     1260                    1280                     130

CTT CAA AAG CTG AAG TCG GCC GTT CCG CTA CCG CTT CCT GTA AAG GAT CGG AAA
 L   Q   K   L   K   S   A   V   P   L   P   L   P   V   K   D   R   K
                         1320                    1340

TCC TTC TTG GGC GCC ACC GTT GGC CTG GGT CCA GCG AGC CTT
 S   F   L   G   A   T   V   G   L   G   P   A   S   L
```

FIG. 4C

```
       1360                1380                1400
GCG GCG GAA CTT CAC GCG ATC GGC AAT GGC GCT GAC TAC GTC CGC ACC CAC GCG CCT
 A   A   E   L   H   A   I   G   N   G   A   D   Y   V   R   T   H   A   P
           1420                1440                1460
GGA GAT CTG CGA AGC GCA ATC ACC ATC TCG GAA ACC CTC GCG AAA TTT CGC AGT CGC
 G   D   L   R   S   A   I   T   I   S   E   T   L   A   K   F   R   S   R
           1480                1500                1520
GAC GCC AGA GAC CGA GGG TTA GAT CAT CAT GCC TAG CATTCACCTTCCGCCCCGCTAGCGGACC
 D   A   R   D   R   G   L   D   H   H   A   *
           1540                1560                1580                1600
CTGGTCAGGTTCCGCGAAGGTGCGCAGACATGCTGGGCTCGTCAGGATCAAACTGCACTATGAGGCGGCGGTT
                1620                1640                1660                1680
CATACCCGCCGCCCAGGGGAGCGGCAATGGACAGCGAGGAGCCTCCGAACGTTCGGCTCGCTGCTCGGGTGATATCGAC
                1700                1720                1740
GAGGTTGTGCGGCGGCTGATGCAACGACGCGCTGCCGGTGATGTCCGCCAAGGGAACGCCCGCCTGGACGTCGCGGCGG
                1760                1780                1800                176
ATCGACCGGACATTCGCGGAGACCTTCGTCCTGAGATCCGAGCTC                               0
```

```
                                                              NcoI
[ATG] ACC ATG ATT ACG CCA AGC TTG CAT GCC TGC AGG TCC [ATG] GTG    pJIT92
                              lacZ                   sul
[ATG] ACC ATG ATT ACG CCA AGC TTG CAT GCC TGC AGG TCC ATG C[AT G]GT G  pJIT92ΔNc
```

FIG. 5B

SULFONAMIDE RESISTANCE GENES AND THEIR USE

This application is a continuation of application Ser. No. 08/102,395, filed Aug. 5, 1993, which is a continuation of Ser. No. 07/985,352 filed Dec. 1, 1992, which is a continuation of Ser. No. 07/746,306, filed Aug. 14, 1991, which is a continuation of Ser. No. 07/429,227, filed Oct. 31, 1989, all abandoned.

This invention relates to sulfonamide resistance genes.

Sulfonamides are anti-bacterial compounds which act as inhibitors of dihydropteroate synthase (DHPS), an enzyme of the folic acid synthesis pathway. Resistance to sulfonamides is conferred on bacteria by various R plasmids in Enterobacteriaceae and is found in transposons such as Tn21 (De La Cruz and Grinsted. J. Bact. 151, 1982, 222–228) and Tn2603 (Yamamoto et al, Mol. Gen. Genet. 181, 1981, 464–469). A sulfonamide resistance gene (sul) codes for a modified DHPS which is insensitive to inhibition by sulfonamides.

According to the present invention, there is provided a method of transforming a cell, which method comprises (i) transforming a plant cell whose growth is sensitive to inhibition by a sulfonamide or a salt thereof with a chimaeric gene comprising (a) a plant promoter, (b) a sulfonamide resistance gene having a sequence encoding a transit peptide fused to the 5'-end of the resistance gene and (c) a plant polyadenylation/terminator sequence;

(ii) selecting a transformed plant cell whose growth is resistant to inhibition by a sulfonamide or salt thereof;

(iii) optionally, regenerating from the transformed plant cell a genetically transformed plant which exhibit the said resistance;

(iv) optionally, obtaining seed from the regenerated plant; and (v) optionally, propagating plants from the seed.

Transformed cells can be selected whose growth is resistant to a predetermined concentration of a sulfonamide, such as asulam, or a salt thereof. Plants which are resistant to asulam and its salts can be regenerated from transformed cells. Asulam is methyl (4-aminobenzenesulphonyl)-carbamate. That resistance of cells or regenerants is due to the integration and expression of the sul gene may be verified by assaying for the presence of sulfonamide-insensitive DHPS.

A DNA fragment suitable for use in the method of the invention comprises a sulfonamide resistance gene having a sequence encoding a transit peptide fused to the 5'-end of the resistance gene. The invention also provides a vector which comprises a chimaeric gene comprising (a) a plant promoter; (b) a sulfonamide resistance gene having a sequence encoding a transit peptide fused to the 5'-end of the resistance gene and (c) a plant polyadenylation/terminator sequence, such that the gene is capable of being expressed in a plant cell transformed with the vector. Plant cells are provided which are transformed with the chimaeric gene.

A transgenic plant according to the invention contains in its cells a chimaeric gene comprising (a) a plant promoter, (b) a sulfonamide resistance gene having a sequence encoding a transit peptide fused to the 5'-end of the resistance gene and (c) a plant polyadenylation/terminator sequence, such that the plant exhibits resistance to a herbicide which acts by inhibiting dihydropteroate synthase. Seed can be obtained from the transgenic plant.

The invention also can be used to kill selectively weeds. The invention provides a method of controlling the growth of weeds at a locus, which method comprises applying an effective amount of a herbicide which acts by inhibiting dihydropteroate synthase to a locus where a transgenic plant of the invention is being cultivated. The herbicide is preferably asulam or an agriculturally acceptable salt thereof.

A sulfonamide resistance gene can also be used as a selectable marker, for example on the basis of the resistance it confers to sulfadiazine, asulam and their salts. A gene encoding another trait of interest can be linked, for example fused, to a sulfonamide resistance gene and introduced into cells. The cells are then grown on a medium containing a sulfonamide or one of its salts. Cells which survive can be assumed to have been transformed not only with the sulfonamide resistance gene but with the other gene as well.

Accordingly, the present invention provides a DNA fragment comprising a sulfonamide resistance and, linked thereto, a gene encoding a second trait such that, when the fragment is used to transform a cell, the expression of sulfonamide resistance by the cell can be utilised as an indicator that the cell has been transformed by both the sulfonamide resistance gene and the gene coding for the second trait. The invention additionally provides a method of transforming a cell, which method comprises:

(i) co-introducing a sulfonamide resistance gene and a gene encoding a second trait into a cell whose growth is sensitive to inhibition by a sulfonamide or a salt thereof; and (ii) selecting a transformed cell whose growth is resistant to inhibition by a sulfonamide or salt thereof. Such a selected cell can then be screened for the presence of the second gene.

The invention further provides a new sulfonamide resistance gene. This gene consists of DNA encoding a mutated DHPS of the sequence:

M V T V F G I L N L T E D S F F D E S R R L D P A G A V T A
A I E M L R V G S D V V D V G P A A S H P D A R P V S P A D
E I R R I A P L L D A L S D Q M H R V S I D S F Q P E T Q R
Y A L K R G V G Y L N D I Q G F P D P A L Y P D I A E A D C
R L V V M H S A Q R D G I A T R T G H L R P E D A L D E I V
R F F E A R V S A L R R S G V A A D R L I L D P G M G F F L
S P A P E T S L H V L S N L Q K L K S A L G L P L L V S V S
R K S F L G A T V G L P V K D L G P A S L A A E L M A I G N
G A D Y V R T H A P G D L R S A I T I S E T L A K F R S R D
A R D R G L D H A;

optionally modified by one or more amino acid insertions and/or deletions and/or by an extension at either or both ends provided that resistance to asulam is conferred on a cell when a gene encoding such a modified sequence is expressed therein.

A preferred gene has the sequence:

```
ATGGTGACGGTGTTCGGCATTCTGAATCTCACCGAGGACTCCTTCTTCGATGAGAGCCGG
CGGCTAGACCCCGCCGGCGCTGTCACCGCGGCGATCGAAATGCTGCGAGTCGGATCAGAC
GTCGTGGATGTCGGACCGGCCGCCAGCCATCCGGACGCGAGGCCTGTATCGCCGGCCGAT
```

-continued

```
GAGATCAGACGTATTGCGCCGCTCTTAGACGCCCTGTCCGATCAGATGCACCGTGTTTCA
ATCGACAGCTTCCAACCGGAAACCCAGCGCTATGCGCTCAAGCGCGGCGTGGGCTACCTG
AACGATATCCAAGGATTTCCTGACCCTGCGCTCTATCCCGATATTGCTGAGGCGGACTGC
AGGCTGGTGGTTATGCACTCAGCGCAGCGGGATGGCATCGCCACCCGCACCGGTCACCTT
CGACCCGAAGACGCGCTCGACGAGATTGTGCGGTTCTTCGAGGCGCGGGTTTCCGCCTTG
CGACGGAGCGGGGTCGCTGCCGACCGGCTCATCCTCGATCCGGGGATGGGATTTTTCTTG
AGCCCCGCACCGGAAACATCGCTGCACGTGCTGTCGAACCTTCAAAAGCTGAAGTCGGCG
TTGGGGCTTCCGCTATTGGTCTCGGTGTCGCGGAAATCCTTCTTGGGCGCCACCGTTGGC
CTTCCTGTAAAGGATCTGGGTCCAGCGAGCCTTGCGGCGGAACTTCACGCGATCGGCAAT
GGCGCTGACTACGTCCGCACCCACGCGCCTGGAGATCTGCGAAGCGCAATCACCATCTCG
GAAACCCTCGCGAAATTTCGCAGTCGCGACGCCAGAGACCGAGGGTTAGATCATGCCTAG;
``` optionally modified by one or more codon insertions and/or deletions and/or by an extension at either or each end provided that resistance to a sulfonamide is conferred on a cell when the modified gene is expressed therein.

A modified gene sequence may be obtained by introducing corresponding changes into the DNA sequence encoding the unmodified amino acid sequence of the sul gene of the invention. This may be achieved by any appropriate technique, including restriction of the DNA sequence with an endonuclease, insertion of linkers, use of an exonuclease and/or a polymerase and site-directed mutagenesis.

A shorter DNA sequence therefore may be obtained by removing nucleotides from the 5'-terminus or the 3'-terminus of the DNA sequence encoding the unmodified amino acid sequence, for example using an exonuclease such as Bal 31. Whether a modified DNA sequence encodes a modified protein capable of conferring resistance to asulam may be readily ascertained. The modified DNA sequence can be cloned into an appropriate plasmid and a host cell transformed and tested for sulfonamide resistance, for example resistance to asulam or sulfadiazine.

As far as extensions are concerned, the amino acid sequence of the sul gene may be extended by up to 70 amino acids at either or both ends. Up to 50 amino acids, for example up to 20 amino acids, may therefore be added to the N-terminus and/or the C-terminus. Such an extension may therefore be, at the N-terminus, a transit peptide sequence. A transit peptide sequence is required when transforming plant cells with the aim of generating plants resistant to herbicides which act by inhibiting dihydropteroate synthase.

Where the sequence of the mutated DHPS encoded by the gene according to the invention is modified, typically there is a degree of homology of at least 70% between the modified and unmodified sequences. For example, the degree of homology may be 85% or more or 90% or more. In any event resistance to asulam, including to an agriculturally acceptable salt thereof, must be conferred on a cell when a gene encoding a modified sequence is expressed in the cell.

For the purposes of amplification, manipulation and transformation, a sulfonamide resistance gene is typically part of a larger DNA fragment. Such larger fragments may be up to 2.0 kb, for example up to 1.25 kb. Such a fragment is typically provided with restriction sits are both ends to facilitate manipulation. It preferably incorporates transcriptional regulatory sequences and/or, if not present at the 3'-end of the coding sequence of the gene, a stop codon for the sulfonamide gene. A fragment may therefore also incorporate a promoter, Shine-Delgarno sequence and terminator sequence which are capable of enabling the sul gene to be expressed in plant cells or in whichever other type of cells are to be transformed by the gene.

The fragment may be a hybrid fragment in which the sul gene promoter has been replaced by another promoter. The promoter may be a plant promoter, for example the 35S cauliflower mossic virus promoter or a nopaline synthase or octopine synthase promoter. Where manipulations in bacteria are undertaken, a bacterial promoter such as the lac promoter may be present.

In one aspect of the invention, plant cells are transformed with a chimaeric sul gene comprising (a) a plant promoter operably linked to (b) a sul gene having a sequence encoding a transit peptide fused to the 5'-end of the said sul gene, and (c) a plant polyadenylation/terminator sequence. Plant cells can be transformed with the chimaeric gene directly, typically by way of a DNA fragment comprising the chimaeric gene. Alternatively, there may be used a vector incorporating the chimaeric gene. The chimaeric gene includes transcriptional control sequences, for example as above, and translational initation and/or termination sequences. A vector typically contains too a region which enables the chimaeric gene to be transferred to and stably integrated in the plant cell genome.

Any sul gene may be employed, although the gene is typically a bacterial gene. The sul gene may be a sulI or sulII gene. A sul gene according to the invention may be employed, although optionally there may be base changes which do or do not result in amino acid substitutions in the expressed product. The sul gene is provided with a transit peptide sequence at its 5'-end. The encoded transit peptide is able to target the modified DHPS encoded by the sul gene into the chloroplast stroma. The chimaeric gene comprising a sul gene having a sequence encoding a transit peptide fused to the 5'-end of the resistance gene is typically prepared by ligating the transit peptide sequence to the 5'-end of the resistance gene. The transit peptide sequence may be the transit peptide for ribulose-1,5-bisphosphate carboxylase/oxygenase (RUBISCO). The pea RUBISCO transit peptide may be employed.

Preferably the sul coding sequence is fused to a transit peptide coding sequence in such a way that cleavage between the transit peptide and the modified DHPS encoded by the sul gene releases the mature modified DHPS into the chloroplast stroma. In other words, the sul gene is not fused to codons encoding the N-terminal amino acid residues of the mature protein which is normally targetted to the chloroplast stroma by the transit peptide. This is in contrast to the targetting efficiency of a fusion between the RUBISCO transit peptide and 5-enolpyruval shikimate phosphate (EPSP). Such a fusion protein is not targetted to the chloroplast stroma when the N-terminal sequence of the mature RUBISCO protein is not present (Comai et al, J. Biol. Chem. 263, 15104–15109, 1988).

Transformed plant cells can be selected by growth in a medium containing a sulfonamide or a salt thereof, such as sulfadiazine, asulam or an agriculturally acceptable salt thereof. Plant tissue can therefore be obtained comprising a plant cell which incorporates a sul gene in the plant cell genome, the gene being expressible in the plant cell. Plants can then be regenerated which include the sul gene in the plant cell genome such that the gene can be expressed. The regenerated plants can be reproduced by conventional means and, for example, seed obtained.

A preferred way of transforming a plant cell is to use *Agrobacterium tumefaciens* containing a vector comprising a chimaeric sul gene as above. A hybrid plasmid vector may therefore be employed which comprises:

(a) the chimaeric gene under the control of regulatory elements capable of enabling the gene to be expressed when integrated in the genome of a plant cell;

(b) at least one DNA sequence which delineates the DNA to be integrated into the plant genome; and (c) a DNA sequence which enables this DNA to be transferred to the plant genome.

Typically the DNA to be integrated into the plant cell genome is delineated by the T-DNA border sequences of a Ti-plasmid. If only one border sequence is present, it must be the right border sequence. The DNA sequence which enables the DNA to be transferred to the plant cell genome is generally the virulence (vir) region of a Ti-plasmid.

The sul gene and its transcriptional and translational control elements can therefore be provided between the T-DNA borders of a Ti-plasmid. The plasmid may be a disarmed Ti-plasmid from which the genes for tumorigenicity have been deleted. The sul gene and its transcriptional and control elements can, however, be provided between T-DNA borders in a binary vector in trans with a Ti-plasmid with a vir region. Such a binary vector therefore comprises:

(a) the chimaeric gene under the control of regulatory elements capable of enabling the gene to be expressed when integrated in the genome of a plant cell; and (b) at least one DNA sequence which delineates the DNA to be integrated into the plant genome.

*Agrobacterium tumefaciens*, therefore, containing a hybrid plasmid vector or a binary vector in trans with a Ti-plasmid possessing a vir region can be used to transform plant cells. Tissue explants such as stems or leaf discs may be inoculated with the bacterium. Alternatively, the bacterium may be co-cultured with regenerating plant protoplasts. Plant protoplasts may also be transformed by direct introduction of DNA fragments which encode the mutated DHPS and in which the appropriate transcriptional and translational control elements are present or of a vector incorporating such a fragment. Direct introduction may be achieved using electroporation, polyethylene glycol, microinjection or particle bombardment.

Plant cells from monocotyledonous or dicotyledonous plants can be transformed according to the present invention. Monocotyledonous species include barley, wheat, maize and rice. Dicotyledonous species include tobacco, tomato, sunflower, petunia, cotton, sugarbeet, potato, lettuce, melon, soybean, canola (rapeseed) and poplars. Tissue cultures of transformed plant cells are propagated to regenerate differentiated transformed whole plants. The transformed plant cells may be cultured on a suitable medium, preferably a selectable growth medium. Plants may be regenerated from the resulting callus. Transgenic plants are thereby obtained whose cells incorporate a sul gene in their genome, the sul gene being expressible in the cells. Seed from the regenerated plants can be collected for future use.

The growth of weeds can be controlled by the use of a herbicide which acts by inhibiting dihydropteroate synthase, such as asulam or an agriculturally acceptable salt thereof, at a locus where plants according to the invention are under cultivation. As these plants are resistant to the herbicide due to expression of a mutated DHPS, the herbicide or a mixture of such herbicides can be applied without fear of damaging the plants. The herbicides may be applied pre- and/or post-emergence of the weeds and/or the plants. Suitable agriculturally acceptable salts include the alkali metal (particularly sodium and potassium), ammonium, amine (particularly diethanolamine, triethanolamine, octylamine, morpholine and dioctylmethylamine) and alkaline earth metal (particularly calcium and magnesium) salts.

Herbicides which act by inhibiting dihydropteroate synthase, such as asulam and its salts, are active against monocotyledonous and dicotyledenous weeds. They exhibit a low toxicity to mammals, birds, fish and wild life in general, and have a short soil persistence. They may be used, for example at rates of application of from 1.0 to 4.0 kg asulam equivalent/hectare, by post-emergence application to control the growth of annual and perennial grass weeds such as:

*Agropyron repens, Agrostis gigantea, Agrostis stolonifera, Alopecurus myosuroides, Avena fatua, Brachiaria eruciformis, Bromus tactorum, Cenchrus pauciflorus, Cynodon dactylon, Digitaria sanguinalis, Digitaria scalarum,* Digitaria spp. *Echinochloa colonum, Echinochloa crus-galli, Eleusine indicia (=africana),* Eragrostis sp, *Hordeum murinum, Holcus lanatus, Imperata cylindrica, Leptochloa filiformis, Panicum fasciculatum, Panicum purpurascens, Paspalum dilatatum, Poa annua, Poa trivialis, Rottboellia exaltate,* Setaria spp and *Sorghum halepense;* and annual and perennial broad-leafed weeds such as:

Ambrosia sp, Anthemis sp, Artemisia sp, *Bellis perennis, Cirsium arvense,* Erigeron sp, *Galinsoga parviflora,* Matricaria spp, *Senecio jacobaea, Sonchus oleraceus, Tussilago farfara, Capsella bursa-pastoris Erysimum cheiranthoides, Raphanus raphanistrum, Sinapis arvensis, Polygonum aviculare, Polygonom convolvulus, Polygonum persicaria, Rumex crispus, Rumex obtusifolius, Equisatum arvensis* and *Pteridium aquilinum.*

The herbicides, in particular asulam and its agriculturally acceptable salts, are normally applied as spray fluids. Such spray fluids may, if desired, contain from 0.1% to 1% w/v of surfactant. Suitable surfactants may be of the ionic or non-ionic types, for example sulphoricinoleates, quaternary ammonium derivatives, products based on condensates of ethylene oxide with nonyl- or octyl-phenols, or carboxylic acid esters of anhydro-sorbitols which have been rendered soluble by etherification of the free hydroxy groups by condensation with ethylene oxide, alkali and alkaline earth metal salts of sulphuric acid esters and sulphonic acids such as dinonyl- and di-octyl-sodium sulpho-succinates and alkali and alkaline earth metal salts of high molecular weight sulphonic acid derivatives, e.g. sodium and calcium ligno-sulphates.

Such spray fluids may be obtained from concentrates comprising asulam or an agriculturally acceptable salt thereof. Compositions in the form of concentrates which are to be diluted, e.g. with water or oil, before use as herbicides may, for example, contain from 0.05% to 10% of surfactant, e.g. from 0.05% to 10% w/w of surfactant in the case of solid concentrates and from 0.05% to 10% w/v of surfactant in the case of liquid concentrates.

Herbicidal compositions containing the herbicide may also contain diluents or carriers and/or, if desired, conventional adjuvants such as adhesives, colouring agents and corrosion inhibitors. These adjuvants may also serve as carriers or diluents. Examples of suitable solid diluents or carriers are water-soluble alkali metal (e.g. sodium or potassium) chlorides (e.g. sodium chloride), carbonates, bicarbonates and sulphates, and urea. The solid compositions, which may take the form of water soluble powders or granules, are preferably prepared by grinding the active ingredient with solid diluents. Granular formulations may be prepared by granulating compositions in powder form obtained as described above.

Liquid compositions may take the form of aqueous solutions or suspensions in oil which may incorporate surfactants. Suitable liquid diluents for incorporation in the liquid compositions include water and aliphatic and aromatic hydrocarbons. Surfactants, which may be present in the liquid compositions, may be of the type described above and may, when liquid, also serve as diluents or carriers. Liquid compositions in the form of concentrates may be diluted with water or an oil, e.g. kerosene, to give compositions ready for use.

A sul gene can also be used as a selectable marker for cell transformations on the basis that cells transformed with the gene are resistant to a sulfonamide such as sulfadiazine, asulam or one of its salts. This applies not only to plant cell transformations but also to transformations of other cells, for example bacteria. A sul gene can be co-introduced with a gene encoding a second trait into cells. The cells are screened for resistance to a sulfonamide or salt thereof. Cells resistant to the sulfonamide or sulfonamide salt are screened for the gene coding for the second trait.

This second trait may be another agriculturally desirable property such as resistance to another herbicide. The second trait may be a trait for which it is difficult to assay. In the context of plants, the sul gene may therefore be linked to a gene coding for a storage protein such as phaseolin; a lectin; a resistance factor against a disease, an insect or another herbicide; or a factor providing tolerance to environmental stress. Any sul gene may be employed; although the gene is typically a bacterial gene. The gene may be a sulI or sulII gene. A sul gene according to the invention may be provided, although optionally there may be base changes which do or do not result in amino acid substitutions in the expressed product. A chimaeric gene as described above is used when the sul gene is being used as a selectable marker for plant cell transformations.

For plant cells, a chimaeric sul gene is provided between T-DNA borders. The gene encoding the second trait of interest is also provided between T-DNA borders. If the two genes are provided between the same T-DNA borders, preferably the chaimeric sul gene is closer to the left border sequence. The gene encoding the second trait of interest is also in the form of a chimaeric gene comprising a plant promoter for the coding sequence and a plant polyadenylation/terminator sequence.

A gene encoding a second trait of interest can, therefore, be introduced with a sul gene into cells whose growth is sensitive to inhibition by a sulfonamide such as sulfadiazine, asulam or an agriculturally acceptable salt thereof. A single DNA fragment containing both genes or two DNA fragments each containing a different one of the genes may be employed. The cells can then be grown in a medium containing the sulfonamide or salt thereof. Cells which survive can be assumed to have been transformed not only with the sul gene but also with the gene encoding the second trait. The genes can be introduced into the cells to be transformed directly or by any appropriate vector, for example a plasmid, phage (for bacteria) or virus.

In the present invention, resistance or sensitivity of cells to a sulfonamide such as sulfadiazine, asulam or one of its salts is assessed by the ability of the cell to grow, to grow less well or not to grow in the presence of a predetermined concentration of the sulfonamide or salt thereof. This concentration may be selected depending upon circumstances. It may be 10, 25, 50, 100, 250 or 500 µg, calculated as the sulfonamide per ml of the medium in which the cells are present. That resistance of cells or regenerants is due to the integration and expression of the sul gene may be verified by assaying for the presence of sulfonamide-insensitive DHPS.

The following Examples illustrate the invention. In the accompanying drawings:

FIGS. 1(A and B) shows the sub-cloning of fragments into pUC vectors. Thick lines represent the sequences originating from plasmid R46, thin lines show the vectors. Small arrows indicate the direction of transcription initiated by the lac promoter. Vectors (pBR322, pUC12, pUC19) were treated with alkaline phosphatase during their digestion with restriction enzymes. $T_4$ DNA ligase was used for ligating a vector and insert or for circularising deleted plasmids. MCS represents multiple cloning sites.

Figure 2:
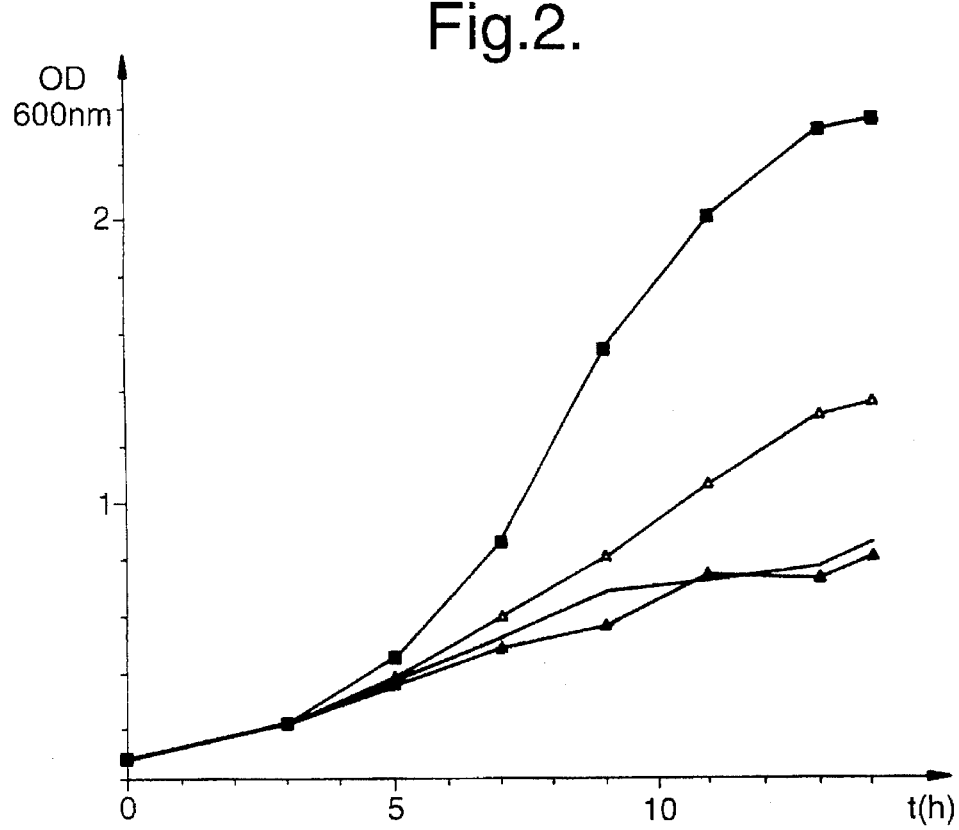

FIG. 2 shows the growth of *E. coli* strain JM101 harbouring various plasmids on minimal medium containing asulam at 500 µg/ml. Bacteria with no plasmid, dots; pUC12sul, closed triangles; pUC19sul, open triangles; and pBRsulΔ3, closed circles.

Figure 3:
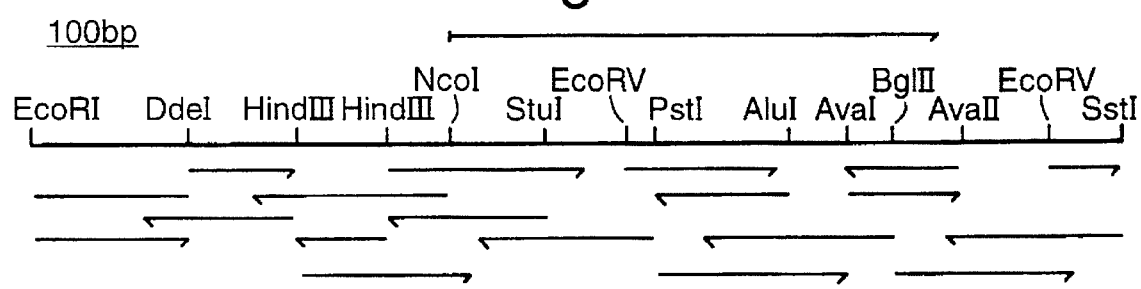

FIG. 3 shows the strategy for sequencing the fragment from pBRsulΔ3 containing the sul gene. The arrows indicate the direction of sequencing. The upper arrow shows the position of the coding sequence. Not all the AluI, AvaII, DdeI sites are indicated.

FIG. 4 shows the nucleotide sequence of the 1.8 kb fragment of plasmid R46 present in pBRsulΔ3. The first start codon of the open reading frame (ORF) and the stop codon are boxed. The putative ribosome-binding-site is in an open box. The predicted amino-acid sequence of the mutated DHPS encoded by the sul gene is shown under the nucleotide sequence.

Figure 5A:
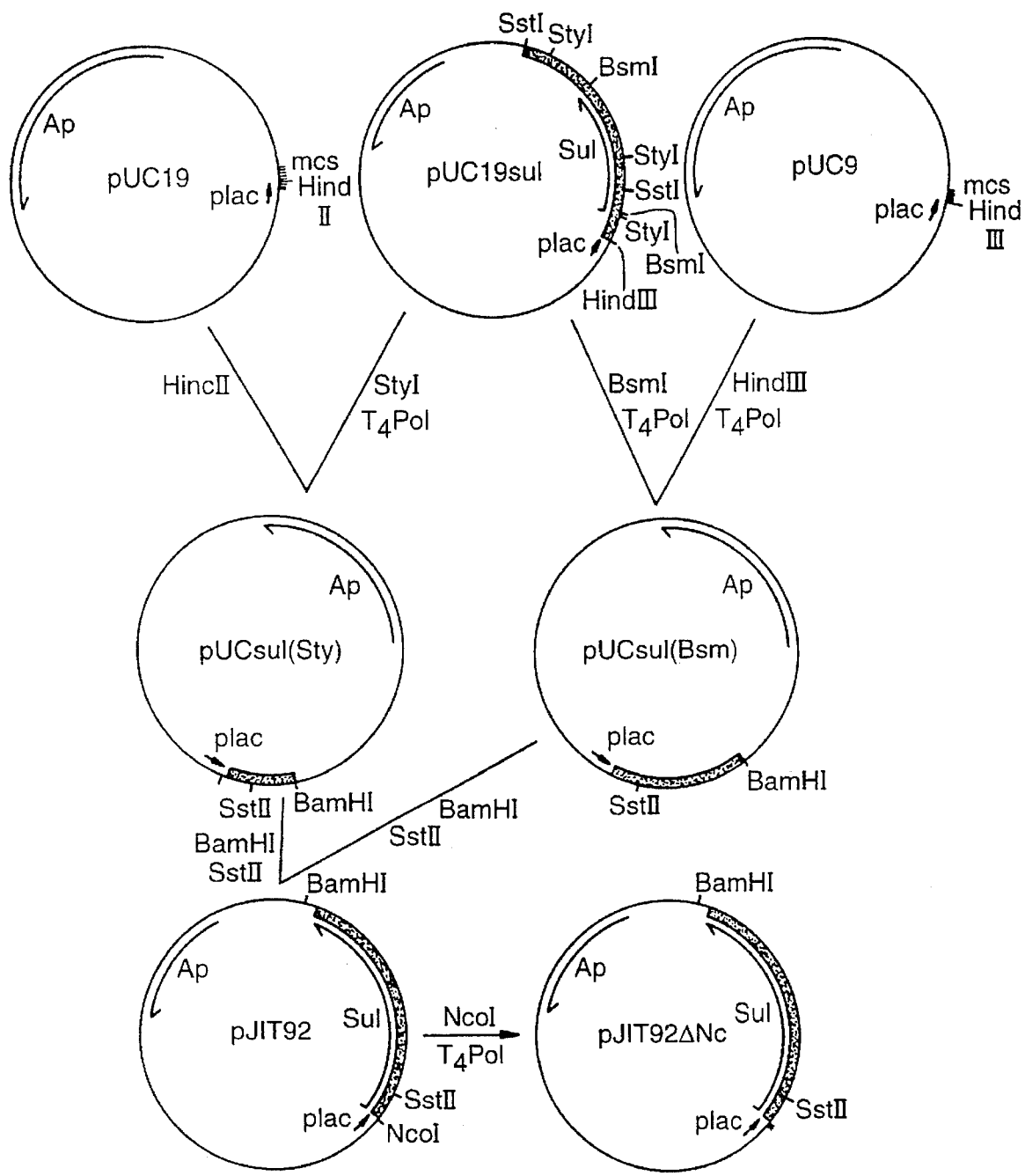

FIGS. 5(A and B) shows the cloning of the sul gene in frame with the lac promoter into pUC19, giving pJIT92. At each step, $T_4$ DNA ligase was used to ligate the fragments of DNA. Vectors were treated with alkaline phosphatase during their digestion with restriction enzymes. The downstream BsmI site in the sul gene includes the stop codon which is eliminated by the $T_4$ DNA polymerase treatment but restored when the BsmI fragment is inserted into a filled-in HindIII site. The nucleotide sequence in the vicinity of the start and stop codons of the sul gene in pJIT92 was checked by sequencing. The sequences indicate the translation frames in pJIT92 and pHJIT92ΔNc. The four extranucleotides inducing the frame shift in pJIT92ΔNc are underlined.

Figure 6:
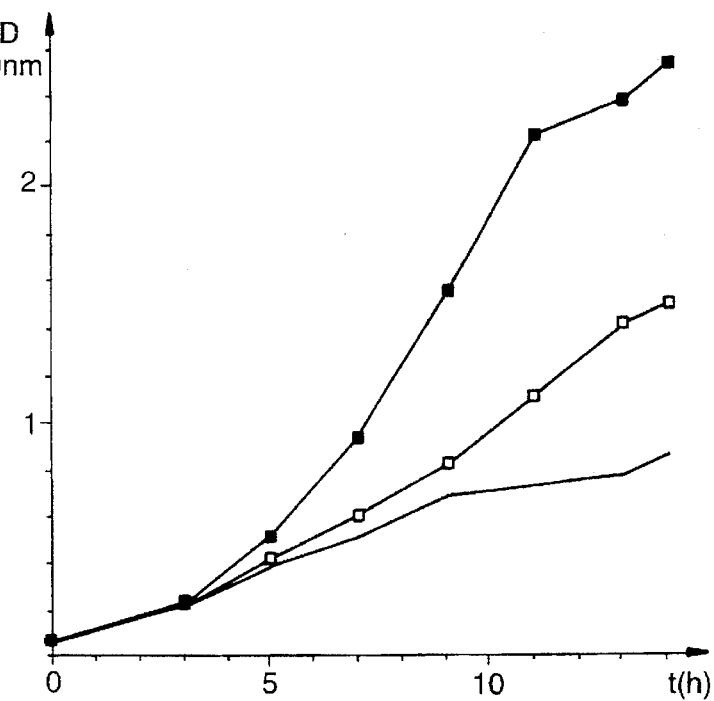

FIG. 6 shows the growth of *E. coli* strain JM101 harbouring no plasmid, dots; pHJIT92, closed squares; and pJIT92ΔNc, open squares; on minimal medium containing asulam at 500 µg/ml.

FIG. 7A shows the organization of pJIT119. A. 35S, CaMV 35S promoter sequence; TP, rbc5 transit peptide sequence; C., CaMV sequence containing transcription terminator and polyadenylation sequence. FIG. 7B. Upper lines: nucleotide and amino acid sequences of rbcS (Anderson and Smith, Biochem J. 240, 709–715, 1986). Arrow indicates the point of cleavage between the transit peptide and the mature protein. Bottom lines: nucleotide and amino acid sequences at the junction between the rbcS transit peptide sequence and the sul coding sequence in pJIT119.

EXAMPLE 1

Isolating and Examining the sul gene (a) Cloning of a fragment of plasmid R46 carrying the sul gene A 1.25 kB HindIII-SstI fragment from within the 2.8 kb EcoR1-SalI fragment of plasmid R46 (Brown and Willette, plasmid, 5, 188-201, 1981) was cloned into pUC vectors (Yanish-Peron et al., Gene 33, 103-119, 1985) as shown in FIG. 1. In brief, the 1.25 kb HindIII-SstI fragment was electroeluted from an agarose gel after cutting with HindIII and SstI. This fragment was ligated to pUC12 or pUC19 cut with the same enzymes to create pUC12sul and pUC19sul respectively.

The ability of pUC12sul and pUC19sul to confer resistance to asulam was assessed by growing *E. coli* JM101 harbouring either plasmid on minimal medium containing 500 µg of asulam per ml. The results are shown in FIG. 2. These show that the 1.25 kb HindIII-SstI fragment does not allow bacteria to grow on asulam at 500 µg/ml when cloned into the HindIII-SstI sites of pUC12 but that the fragment does allow bacteria to grow on asulam at 500 µg/ml when cloned into the same sites of pUC19.

These data indicate that the sul gene is orientated from the HindIII site towards the SstI site in the HindIII-BstI fragment and that this fragment contained the coding sequence or an essential part of it, but not all the information required for the expression of the gene. The lac 5' sequence is thought to replace the equivalent sul sequence missing in pUC19sul.

Plasmid pBRsulΔ1 was obtained by deleting 550 bp from the EcoRI end of the 2.8 kb EcoRI-SalI fragment of R46 using BAL31 and by cloning the resulting fragment into pBR322 as shown in FIG. 1. The EcoRI-ClaI fragment from pBR322, containing the -35 sequence of the $TC^r$ promoter, was deleted in pBKsulΔ1 to give pBRsulΔ2. A 300 bp SstI-SalI fragment was deleted at the other extremity of the R46 sequence remaining in pBRsulΔ2, giving pBRsulΔ3. The growth of *E. coli* JM101 harbouring pBKsulΔ3 in minimal medium containing asulam at 500 µg/ml is shown in FIG. 2. This indicates that none of the deletions affect the resistance to asulam. Consequently, the 1.8 kb sequence remaining in pBRsulΔ3 contains all the information required for the expression of the sul gene.

(b) Nucleotide sequencing

The strategy used to determine the nucleotide sequence of the 1.8 kb fragment from R46 remaining in pBRsulΔ3 is shown in FIG. 3. The sequence was determined using the dideoxy chain extension method (Sanger et al., Proc. Natl. Acad. Sci. USA 74, 5463-5467, 1977) as described by Mullineaux et al., (EMBO J., 3, 3063-3068, 1984), except that [$^{35}$S]daTP was used for radiolabelling. In some cases, dITP and Sequenase (United States Biochemical Corp.) were used in the reactions instead of dGTP and Klenow polymerase. The sequence is presented in FIG. 4. An open reading frame (ORF) of 840 bp, preceded by a putative Shine and Delgarno sequence, was present in the sequence.

(c) Expression of the sul gene

The putative coding sequence was recovered from pUC19sul and placed in frame with the first codons of the lacZ gene in pUC19, to form pJIT92 as shown in FIG. 5. This was achieved as follows. pUC19sul was cut with StyI. After treatment with $T_4$ polymerase to fill in the ends, the small fragment containing the sul start codon was eluted from an agarose gel and cloned into the HindIII site of pUC19, giving pUCsul(Sty), in which the lacZ ATG and the sul ATG are in frame. The BsmI fragment of pUC19sul was eluted from an agarose gel after treatment with $T_4$ polymerase and cloned into the filled-in HindIII site of pUC9, giving pUCsul(Bsm).

The sul stop codon present in the BsmI site is thus restored by the HindIII (confirmed by sequencing). To reconstruct the entire sul gene, the SstII-BamHI fragment from pUCsul(Bsm) was inserted into the same sites of pUCsul(sty), creating pJIT92, which contains the entire sul coding sequence in frame with the lacZ first codons. *E. coli* JM101 harbouring pJIT92 were deposited at the National Collection of Industrial and Marine Bacteria, Aberdeen, GB on 26 Oct. 1989 under accession number NCIMB 40218.

A frame shift was created between the lacZ ATG and the sul ATG, creating pJIT92ΔNc. This was achieved by cutting pJIT92 with NccI, followed by treatment with $T_4$ polymerase and self-ligation so that four bases were added between the lacZ and sul start codons. The frame shift is shown in FIG. 5.

Asulam resistance was determined as in (a) above. The results are shown in FIG. 6. These indicate that the expression of the sul gene was driven by the lac promoter in pJIT92. Translation of the mRNA would lead to the synthesis of the predicted protein when initiated at the sul ATG and of a fusion protein when initiated at the lacZ ATG.

The frame shift present in pJIT92ΔNc reduced the level of resistance to asulam to a level close to the one induced by pUC19sul. The frame shift would have resulted in the synthesis of an abnormal protein when the translation was initiated at the lacZ ATG. In some cases, the translation may have been initiated at the sul ATG, generating a certain amount of functional protein. This would explain the residual resistance to asulam of bacteria having pJIT91ΔNc as seen in FIG. 6. These results confirm that the ORF recovered from pUC19sul coded for sulphonamide resistance.

(d) Analysis of the protein sequence

The amino acid sequence of the mutated DHPS was dedeuced from the nucleotide sequence shown in FIG. 4. The predicted protein contained 279 amino acids and its molecular weight is 30106. The protein possesses a hydrophobic —$NH_2$ end and a hydrophilic —COOH end. The amino acid sequence showed no significant homology with the 4931 sequences present in the PIR data base (release 15.0) of the National Biomedical Research Foundation (Aberdeen, GB).

EXAMPLE 2

Plant Transformation

1. Material and methods (a) Molecular cloning

In a first step to constructing pJIT119, the sul coding sequence was recovered from pJIT92 and inserted into the polylinker of pJIT117 (Guerineau et al., Nucleic Acids Res. 16, 11380, 1988). pJIT92 was cut with NcoI, treated with $T_4$ polymerase, cut with SalI and the digested fragments were separated by electrophoresis in an agarose gel. The fragment containing the sul gene was eluted from the gel as described in Maniatis et al. (Molecular Cloning—A Laboratory Manual, Cold Spring Harbor Laboratory Press, New York, 1982) and ligated to pJIT117 previously cut with SphI, treated with $T_4$ polymerase and cut with SalI, creating pJIT118. The nucleotide sequence at the cloning junction was checked after subcloning a HindIII-PstI fragment carrying the junction into M13mp18 (Yanisch-Perron et al., 1985). The nucleotide sequence was determined by the dideoxy-chain extension method (Sanger et al., 1977).

pJIT58 was constructed by insertion of the gus coding sequence recovered from pBI101-2 (Jefferson et al., EMBO J. 6 3901–3907, 1987), into pJIT30. pJIT30 is an expression cassette made of a pUC-derived vector carrying the sequence from CaMV Cabb-JI corresponding to coordinates 7040–7432 (Franck et al., Cell 21, 285–294, 1980) and containing the 35S promoter, a polylinker and the sequence 7435 to 126 from CaMV providing a polyadenylation signal. The fusion 35S-gus-poly A was moved from pJIT58 into the polylinker of pBIN19 (Bevan, Nucleic Acids Res. 12, 8711–8721 1984) as a KpnI-XhoI fragment, generating pJIT59.

Figure 7:
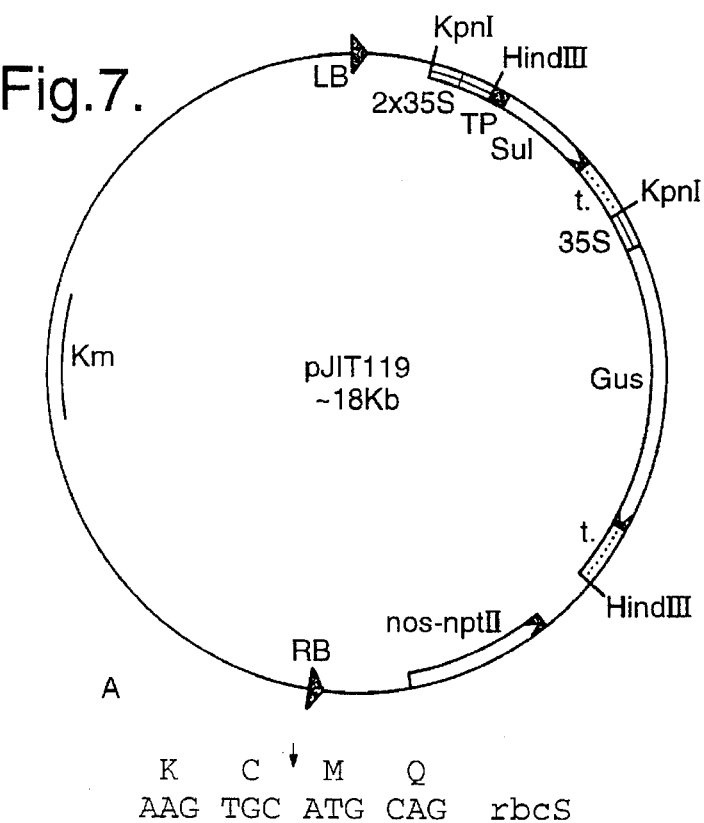

The fusion 35S promoter-rbcS transit peptide (TP)-sul-polyadenylation sequence was recovered from pJIT118 as a KpnI fragment and cloned into the KpnI site of pJIT59, upstream from the gus gene, giving pJIT119. The organisation of pJIT119 is shown in FIG. 7. pGEMTPSUL was constructed by insertion of the fusion transit peptide-sul recovered from pJIT118 as a HindIII-EcoRI fragment, into the polylinker to pGEM-4Z (Promega). *E. coli* JM101 harbouring pJIT119 was deposited at the National Collection of Industrial and Marine Bacteria, Aberdeen GB on 26 Oct. 1989 under accession number NCIMB 40219.

(b) Chloroplast import experiments

The sul and TP-sul genes cloned into pGEM-4Z were transcribed under SP6 RNA polymerase, and capped transcripts were translated in a wheat-germ lysate in the presence of [$^{35}$S]-methionine (Anderson et al., Methods Enzymol. 101, 635–644, 1983; Malton et al., Nucleic Acids Res. 12, 7035–7056, 1984). The translation products were incubated with isolated pea leaf chloroplasts as described (Robinson and Ellis, Eur. J. Biochem. 152, 67–73, 1985). After import, the chloroplasts were incubated with trypsin to digest non-imported proteins, and the organelles were fractionated into stromal and membrane samples. Samples were analysed by sodium dodecyl sulphate (SDS)-polyacrylamide gel electrophoresis followed by fluorography.

(c) Plant transformation

*Nicotiana tabacum* cv Samsun plants were grown in a glasshouse under standard conditions. Approximately 1 cm$^2$ leaf pieces were cut from surface sterilized leaves and floated on MS medium (Murashige and Skoog, Physiol. Plant 15, 473–497, 1962) containing 3% sucrose, 1 mg/l 6-benzylaminopurine (BAF), 0.1 mg/l α-naphthaleneacetic acid (NAA) and 3 mM 2-[N-morpholino]-ethanesulfonic acid (NES), pH 5.7. Bacteria obtained from overnight cultures of *Agrobacterium tumefaciens* strain LBA4404 (Hoekema et al., Nature 303, 179–180, 1983) containing pJIT59 or pJIT119, were centrifuged and resuspended in the same volume of MS medium. One teeth of volume was added to the floating leaf pieces.

Cocultivation was carried out for three days at 25° C. under light (Photoperiod 16 h/8 h). Leaf pieces were blotted dried onto absorbing paper and placed on MS medium as above but containing 0.8% agar, 500 µg/ml of ampicillin, 250 µg/ml cefotaxime and the selective agent at various concentrations. Asulam or sulfadiarine was used for selecting transfrmants.

After one month culture, shoots, developed on leaf pieces placed on selective media, were cut off and rooted on 0.5×MS medium containing 1% sucrose, 1% agar, 3 mM MES pH 5.7, 200 µg/ml amplicillin, 100 µg/ml cefotaxime and eventually sulfadiazine as indicated. Plantlets were transferred to soil when rooted, generally after a month, and grown until seeds could be harvested. Seeds were sterilized in 10% (vol) Domestos (Trade Mark) for 15 min and washed four times in sterile distilled water. Germination took place in Petri diskes containing 0.5×MS medium supplemented with 1% sucrose, 1% agar and sulfadiazine as indicated in the text.

(d) Plant DNA extraction and analysis

Plantlets were ground in 2 ml of grinding buffer (Tris 100 mM pH 8, ethylene diamine tetracetic acid (EDTA) 20 mM, SDS 0.1%, diethyldithiocarbamate 0.5%) per g fresh weight of tissue. Two extractions with one volume of water-saturated phenol/chloroform (1 vol/1 vol) were carried out and nucleic acids were ethanol precipitated. Pellets were dissolved in one ml/g of distilled water and one volume of a solution containing 13% polyethyleneglycol (PEG) 6000 and 0.8M NaCl was added to the aqueous phase. Precipitate was allowed for 30 min at 0° C. DNA was recovered by centrifugation for 5 min at 10000 g. Pellets were washed with 70% ethanol, dried and dissolved in distilled water. DNA concentration was determined using the fluorimetric method as described by Thomas and Farquhar (Anal. Biochem. 89, 35–44, 1978).

For analysis, 10 µg of DNA was digested overnight with 100 units of EcoRI and electrophoresed through a 0.8% agarose gel. The gel was processed and DNA was blotted onto nitrocellulose membrance as described in Maniatis et al. (1982). Prehybridization was carried out for 3 h at 65° C. in 5× SSC (1× SSC is 15 mM sodium citrate, 150 mM NaCl), 25 mM sodium phosphate buffer pH 6.5, 0.1% SDS, 5 mM EDTA, 5× Denhart solution (1× Denhart solution is 0.02% Ficoll, 0.02% polyvinylpyrrolidone (PVP), 0.02% bovine serum albumin (BSA)), 100 µg/ml denatured calf thymus DNA. 35 ng of sul DNa fragment was labelled with [$^{32}$P]dCTP using the random oligonucleotide priming method (Feinberg and Vogelstein, Anal. Biochem. 132, 6–13, 1983) to a specific activity higher than 10$^5$ counts per minute (CPM)/µg. Hybridization was carried out overnight at 65° C. in the prehybridization solution. The membrane was washed in 2× SSC, 0.1% SDS for 30 min at room temperature, then in 2× SSC, 0.1% SDS for 30 min at 65° C., then twice in 0.1× salt and sodium citrate (SSC), 0.1% SDS, for 30 min at 65° C. The membrane was exposed to preflashed X-ray film for 2 days.

2. Results (a) Construction of pJIT119 containing a sul chimeric gene

In order to target the bacterial DHPS to chloroplasts, the sul coding sequence was fused to the pea ribulose bisphosphate carboxylase/oxygenase (rbcS) transit peptide sequence contained in the expression cassette pJIT117 (Guerineau et al., 1988). The fusion was made so that the sul ATG translation initiation codon was exactly in the same position as the mature rbcS ATG in the native enzyme (FIG. 7). The bacterial DHPS was expected to be released from the transit peptide in the chloroplast stroma, in the same form as it is synthesized in bacterial, i.e. not as a fusion protein. For transcription of the chimeric gene, a CaMV 35S promoter with a duplicated enhancer region and CaMV gene VI polyadenylation signal were placed at the 5' and 3' ends respectively of the TP-sul coding sequence. In the final construct used for plant transformation, the chimeric sul gene was inserted between the right and the left T-DNA border of the binary vector pBIN19 (Bevan, 1964) which also carried the chimaeric uida gene (β-glucuronidase (gus)) gene (Jefferson et al., 1966) placed under control of the 35S promoter (FIG. 7). The construct was mobilized into *Agrobacterium tumefaciens* disarmed strain LBλ4404 (Hoekman et al., 1983) using the helper plasmid pRK2013.

(b) In vitro transport of DHPS into isolated chloroplasts

In order to confirm that the rbcS transit peptide is capable of targetting DHPS into chloroplasts, we tested whether chloroplasts are capable of importing the fusion protein (in vitro). The portein (TP DHPS) was synthesized by the in vitro transcription followed by translation in a wehat-germ lysate. This expression system generated TP-DHPS and also a protein of lower $M_r$. The latter corresponds to mature-sized DHPS which is probably generated by internal initiation; a polypeptide of identical $M_r$ was synthesized if DHPS cDNA is expressed by this method.

TF-DHPS was imported into the stroma of isolated pea chloroplasts and processed to a lower $M_r$ form. The processed protein had a mobility similar to that of mature-sized DHPS, suggesting that the entire pre-sequence had been removed. In control experiments (not shown), it was found that mature-sized DHPS (lacking the transit peptide sequence) was not important by chloroplasts under these conditions. These data show that the rbcS RUBISCO transit peptide sequence effectively targets DHPS into the chloroplast stroma.

(c) Transformation of tobacco leaf explants with pJIT119

During preliminary experiments, our sul gene was placed under control of the CaMV 35S promoter and transferred to tobacco plants. Although evidence was obtained that the gene was transcribed, no increase in the level of resistance to sulfonamides was recorded in transformed leaf tissues (data not shown).

Tobacco leaf pieces were then cocultivated with *Agrobacterium tumefaciens* strain LBA4404 carrying pJIT119, and placed on medium containing 50 μg/ml of kanamycin. No shoots developed on untreated control laser pieces whereas a number of shoots grew on cocultivated leaf pieces. Shoots were rooted and assayed for β-glucuronidase (GUS) activity. Leaf pieces from four of the plantlets showing GUS activity and from an untransformed control were placed on medium containing various concentrations of sulfadiazine.

No shoots developed on untransformed control leaf pieces after three weeks on sulfadiazine at 5 μg/ml, whereas shoots developed on leaf pieces prepared from three of the plantlets showing GUS activity, on medium containing up to 500 μg/ml of sulfadiazine. These data indicate that a high level of resistance to sulfadiazine was present in leaf tissue of plantlets displaying GUS activity after cocultivation with *Agrobacterium tumefaciens* carrying pJIT119.

(d) Direct selection of transformants or sulfonamides

To determine if the level of resistance to sulfadiazine recorded in shoots selected on kanamycin was sufficient to allow direct selection of transformants, tobacco leaf explants were cocultivated with *Agrobacterium tumefaciens* carrying pJIT119 and placed on medium containing asulam or sulfadiazine at 100 μg/ml. This value was chosen because untransformed leaf explants did not produce any shoots for one month, on medium containing that concentration.

In a first experiment, asulam was used as the sole selective agent. Shoots developed on leaf explants cocultivated with Agrobacterium harbouring pJIT119 but not on those treated with bacteria carrying pJIT59, a pBIN19 derivative carrying the gus gene but not having the sul gene. Seven shoots growing on leaf explants cocultivated with Agrobacterium carrying pJIT119 were rooted and plants were regenerated. DNA was extracted from plantlets grown from seeds of each of the selected plants and probed for the presence of the bacterial sul gene. Progeny of all seven plants was shown to contain the bacterial sequence, indicating that the shoots selected on asulam were transformants.

In a second experiment, sulfadiazine was used as the sole selective agent. Nine shoots selected on leaf explants cocultivated with Agrobacterium harbouring pJIT119 were placed on rooting medium containing sulfadiazine at 100 μg/ml. Eight rooted and grew normally and one did not. All shoots showed specific GUS activity higher than 100 times the background activity of untransformed material. None of twelve untransformed control shoots rooted and their growth was completely inhibited on sulfadiazine at the same concentration.

In a third experiment, fifteen shoots selected on asulam were placed on rooting medium containing 100 μmg/ml of sulfadiazine. Three did not produce any roots, did not grow and turned yellow, one grew very slowly and produced only one root, eleven grew and rooted normally. GUS assays on rooted shoots showed that ten out of twelve had high GUS activity. Leaf pieces from the two rooted plantlets not showing any GUS activity were challanged on sulfadiazine at 100 μmg/ml. They both produced shoots normally whereas untransformed controls bleeched, suggesting that the sul gene was expressed in those two selected shoots although the gus gene was not. These three experiments demonstrated that the direct selection on sulfonamides, of transformed shoots on leaf explants after transformation with pJIT119, was efficient.

(e) Analysis of the progeny of transformed plants

Seeds harvested from two self-fertilized transformed plants during the first selection experiment and seeds from an untransformed control plant, were germinated on medium containing various concentrations of sulfadiazine. Seedlings from the untransformed seeds died soon after germination, 20 μg/ml of sulfadiazine and more, whereas transformed seedlings developed normally on sulfadiazine at concentrations up to 200 μg/ml. The growth of transformed seedlings was slightly reduced on sulfadiazine at 500 μg/ml.

In order to record the pattern of segregation of the introduced character, seeds from the seven transformed plants obtained during the first selection experiment were germinated on sulfadiazine at 100 μg/ml. Growth was monitored for two weeks. Seedlings developed normally from the seed harvested on 5 out of 7 transformed plants. The segregation of sulfonamide resistance is shown in Table 1.

TABLE 1

| Plant | Number of seeds | | Ratio |
| | resistant | sensitive | |
| --- | --- | --- | --- |
| 1 | 117 | 38 | 3.1/1 |
| 2 | 120 | 34 | 3.5/1 |
| 3 | 76 | 24 | 3.2/1 |
| 4 | 77 | 23 | 3.2/1 |
| 5 | 68 | 32 | 2.1/1 |

The segregation patterns were in most cases three to one which is to be expected from a dominant character encoded by a determinant integrated into the genome at one locus. No difference in the growth of seedlings on sulfadiazine, indicating homozygotic or heterozygotic status, even at 500 μg/ml, could be observed. In contrast, GUS assays allowed a clear distinction between seedlings having one or two alleles of the inserted T-DNA (data not shown). No seedling grew on sulfadiazine at 100 μg/ml, from the seed harvested on two out of the seven transformed plants. However, in both cases, approximately 75% of the seedlings had formed yellow or even green cotyledons, after one month on media containing sulfadiazine at 100 μg/ml. A very low GUS activity, although significantly higher than the activity of untransformed control seedlings, was detected in some of the seedlings. This seemed to indicate that the sul and the gus genes were only very weakly expressed in the progeny of these two plants.

Overall, these data indicate that the sulfonamide resistance gene was transmitted to the progeny of transformed plants and was expressed as a dominant character.

We claim:

1. A plant cell whose growth is resistant to inhibition by a sulfonamide or a salt thereof, which plant cell has been obtained by:
   (i) transforming a plant cell whose growth is sensitive to inhibition by said sulfonamide or a salt thereof with a chimaeric gene comprising (a) a plant promoter, (b) a a sul gene which encodes a modified dihydropteroate (DHPS) conferring sulfonamide resistance, or a sequence having at least 70% homology thereto conferring sulfonamide resistance and which has a sequence encoding a transit peptide cleavable from the modified DHPS fused to the 5'-end of the resistance gene and (c) a plant polyadenylation/terminator sequence wherein (a), (b) and (c) are operably linked; and
   (ii) selecting a transformed plant cell whose growth is resistant to inhibition by said sulfonamide or salt thereof.

2. A cell according to claim 1, wherein the promoter of the chimaeric gene is selected from the 35S cauliflower mosaic virus promoter or a nopaline synthase promoter or octopine synthase promoter.

3. A cell according to claim 1, wherein the chimaeric gene encodes a modified DHPS having the amino acid sequence;

MVT VF GI LNL T E D S F F D E S R R L D P AG AVT A

AI E ML R V G S D V V D V G P A A S H P D A R P V S P A D

E I R R I A P L L D A L S D Q M H R V S I D S F Q P E T Q R

Y AL K R G V G Y L N D I Q G F P D P A L Y P D I A E A D C

R L V V M H S A Q R D G I A T R T G H L R P E D A L D E I V

R F F E A R V S A L R R S G V A A D R L I L D P G M G F F L

S P A P E T S L H V L S NL Q K L K S AL GL P L L V S V S

R K S F L G AT V G L P V K D L G P A S L A A E L H A I G N

G A D Y V R T H A P G D L R S A I TI S E T L A K F R S R D

A R D R G L D H A or at least 70% homology to said sequence provided that resistance to a said sulfonamide is conferred on the cell when the said gene is expressed therein.

4. A cell according to claim 3, wherein the said gene has the DNA sequence;

or at least 70% homology to said sequence modified by one or more codon insertions and/or deletions provided that resistance to a said sulfonamide is conferred on the cell when the said gene is expressed therein.

5. A cell according to claim 1, wherein the transit peptide sequence of the chimaeric gene encodes the transit peptide for ribulose-1,5-bisphosphate carboxylase/oxygenase.

6. A cell according to claim 1, wherein the said sulfonamide is asulam.

7. A transgenic plant exhibiting resistance to a sulfonamide or a salt thereof, which plant contains in its cells a chimaeric gene comprising (a) a plant promoter (b) a sul gene which encodes a modified DHPS conferring sulfonamide resistance, or a sequence having at least 70% homology thereto conferring sulfonamide resistance and which has a sequence encoding a transit peptide cleavable from the modified DHPS fused to the 5'-end of the resistance gene and (c) a plant polyadenylation/terminator sequence wherein (a), (b) and (c) are operably linked.

8. A plant according to claim 7 wherein the promoter of the chimaeric gene is selected from the 35S cauliflower mosaic virus promoter or a nopaline synthase promoter or octopine synthase promoter.

9. A plant according to claim 7 wherein the chimaeric gene encodes a modified DHPS having the amino acid sequence;

MVT VF GI LNL T E D S F F D E S R R L D P AG AVT A

AI E ML R V G S D V V D V G P A A S H P D A R P V S P A D

E I R R I A P L L D A L S D Q M H R V S I D S F Q P E T Q R

Y AL K R G V G Y L N D I Q G F P D P A L Y P D I A E A D C

R L V V M H S A Q R D G I A T R T G H L R P E D A L D E I V

R F F E A R V S A L R R S G V A A D R L I L D P G M G F F L

S P A P E T S L H V L S NL Q K L K S AL GL P L L V S V S

R K S F L G AT V G L P V K D L G P A S L A A E L H A I G N

G A D Y V R T H A P G D L R S A I TI S E T L A K F R S R D

A R D R G L D H A or at least 70% homology to said sequence provided that resistance to a said sulfonamide is conferred on the plant when the said gene is expressed therein.

10. A plant according to claim 9 wherein the said gene has the DNA sequence;

```
ATGGTGACGGTGTTCGGCATTCTGAATCTCACCGAGGACTCCTTCTTCGATGAGAGCCGG
CGGCTAGACCCCGCCGGCGCTGTCACCGCGGCGATCGAAATGCTGCGAGTCGGATCAGAC
GTCGTGGATGTCGGACCGGCCGCCAGCCATCCGGACGCGAGGCCTGTATCGCCGGCCGAT
GAGATCAGACGTATTGCGCCGCTCTTAGACGCCCTGTCCGATCAGATGCACCGTGTTTCA
ATCGACAGCTTCCAACCGGAAACCCAGCGCTATGCGCTCAAGCGCGGCGTGGGCTACCTG
AACGATATCCAAGGATTTCCTGACCCTGCGCTCTATCCCGATATTGCTGAGGCGGACTGC
AGGCTGGTGGTTATGCACTCAGCGCAGCGGGATGGCATCGCCACCCGCACCGGTCACCTT
CGACCCGAAGACGCGCTCGACGAGATTGTGCGGTTCTTCGAGGCGCGGGTTTCCGCCTTG
CGACGGAGCGGGGTCGCTGCCGACCGGCTCATCCTCGATCCGGGGATGGGATTTTTCTTG
AGCCCCGCACCGGAAACATCGCTGCACGTGCTGTCGAACCTTCAAAAGCTGAAGTCGGCG
TTGGGGCTTCCGCTATTGGTCTCGGTGTCGCGGAAATCCTTCTTGGGCGCCACCGTTGGC
CTTCCTGTAAAGGATCTGGGTCCAGCGAGCCTTGCGGCGGAACTTCACGCGATCGGCAAT
GGCGCTGACTACGTCCGCACCCACGCGCCTGGAGATCTGCGAAGCGCAATCACCATCTCG
GAAACCCTCGCGAAATTTCGCAGTCGCGACGCCAGAGACCGAGGGTTAGATCATGCCTAG
```

```
ATGGTGACGGTGTTCGGCATTCTGAATCTCACCGAGGACTCCTTCTTCGATGAGAGCCGG
CGGCTAGACCCCGCCGGCGCTGTCACCGCGGCGATCGAAATGCTGCGAGTCGGATCAGAC
GTCGTGGATGTCGGACCGGCCGCCAGCCATCCGGACGCGAGGCCTGTATCGCCGGCCGAT
GAGATCAGACGTATTGCGCCGCTCTTAGACGCCCTGTCCGATCAGATGCACCGTGTTTCA
ATCGACAGCTTCCAACCGGAAACCCAGCGCTATGCGCTCAAGCGCGGCGTGGGCTACCTG
AACGATATCCAAGGATTTCCTGACCCTGCGCTCTATCCCGATATTGCTGAGGCGGACTGC
AGGCTGGTGGTTATGCACTCAGCGCAGCGGGATGGCATCGCCACCCGCACCGGTCACCTT
CGACCCGAAGACGCGCTCGACGAGATTGTGCGGTTCTTCGAGGCGCGGGTTTCCGCCTTG
CGACGGAGCGGGGTCGCTGCCGACCGGCTCATCCTCGATCCGGGGATGGGATTTTTCTTG
AGCCCCGCACCGGAAACATCGCTGCACGTGCTGTCGAACCTTCAAAAGCTGAAGTCGGCG
TTGGGGCTTCCGCTATTGGTCTCGGTGTCGCGGAAATCCTTCTTGGGCGCCACCGTTGGC
CTTCCTGTAAAGGATCTGGGTCCAGCGAGCCTTGCGGCGGAACTTCACGCGATCGGCAAT
GGCGCTGACTACGTCCGCACCCACGCGCCTGGAGATCTGCGAAGCGCAATCACCATCTCG
GAAACCCTCGCGAAATTTCGCAGTCGCGACGCCAGAGACCGAGGGTTAGATCATGCCTAG
``` or at least 70% homology to said sequence provided that resistance to a said sulfonamide is conferred on the plant when the said gene is expressed therein.

11. A plant according to claim 7 wherein the transit peptide sequence of the chimaeric gene encodes the transit peptide for ribulose-1,5-bisphosphate carboxylase/oxygenase.

12. A plant according to claim 7 wherein the said sulfonamide is asulam.

13. Seed obtained from a transgenic plant as claimed in claim 7.

14. A method of controlling the growth of weeds at a locus where a transgenic plant as claimed in claim 7 is being cultivated, which method comprises applying to the locus an effective amount of a sulfonamide or salt thereof, as herbicide, which acts by inhibiting dihydropteroate synthase.

15. A method of treating a locus in which transgenic plants as claimed in claim 7 are being cultivated, which comprises applying to the locus an effective amount of a sulfonamide or a salt thereof, as herbicide, which acts by inhibiting dihydropteroate synthase.

16. A plant cell according to claim 1, wherein said plant cell is a dicotyledonous plant cell.

17. A plant cell according to claim 1, wherein said plant cell is a monocotyledonous plant cell.

18. A transgenic plant according to claim 7, wherein said transgenic plant is a dicotyledounous plant.

19. A transgenic plant according to claim 7, wherein said transgenic plant is a monocotyledonous plant.

20. A transgenic tobacco plant exhibiting resistance to a sulfonamide or a salt thereof which tobacco plant contains in its cells a chimaeric gene comprising (a) a plant promoter (b) a sul gene which encodes a modified DHPS conferring sulfonamide resistance or a sequence having at least 70% homology thereto, and which has a sequence encoding a transit peptide cleavable from the modified DHPS fused to the 5'-end of the resistance gene and (c) a plant polyadenylation/terminator sequence, wherein (a), (b) and (c) are operably linked.

21. A transgenic oilseed rape plane exhibiting resistance to a sulfonamide or a salt thereof which oilseed rape plant contains in its cells a chimaeric gene comprising (a) a plant promoter (b) a sul gene which encodes a modified DHPS conferring sulfonamide resistance or a sequence having at least 70% homology thereto, and which has a sequence encoding a transit peptide cleavable from the modified DHPS fused to the 5'-end of the resistance gene and (c) a plant polyadenylation/terminator sequence, wherein (a), (b) and (c) are operably linked.

* * * * *

UNITED STATES PATENT AND TRADEMARK OFFICE
CERTIFICATE OF CORRECTION

PATENT NO. : 5,633,444

DATED        : May 27, 1997

INVENTOR(S) : Jean F. Guerineau et al.

It is certified that error appears in the above-identified patent and that said Letters Patent is hereby corrected as shown below:

TITLE PAGE:

Please change the Assignee from "Rhone-Poulenc Agrochimie Limited" to --Rhone-Poulenc Agrochimie--.

Signed and Sealed this

Fourteenth Day of April, 1998

Attest:

BRUCE LEHMAN

*Attesting Officer*    *Commissioner of Patents and Trademarks*